(12) United States Patent
Fender et al.

(10) Patent No.: US 6,630,132 B2
(45) Date of Patent: Oct. 7, 2003

(54) UV-LIGHT-ABSORBING QUATERNARY POLYSILOXANES

(75) Inventors: Michael Fender, Flieden (DE); Manfred Krakenberg, Essen (DE); Holger Leidreiter, Hattingen (DE); Sascha Oestreich, Essen (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 10/217,000

(22) Filed: Aug. 12, 2002

(65) Prior Publication Data

US 2003/0108494 A1 Jun. 12, 2003

(30) Foreign Application Priority Data

Aug. 23, 2001 (DE) .......................... 101 41 356

(51) Int. Cl.[7] .............. A61K 7/42; A61K 7/44; A61K 7/00; A61K 37/74
(52) U.S. Cl. .......... 424/59; 424/60; 424/78.02; 424/400; 424/401
(58) Field of Search .............. 424/59, 60, 78.02, 424/400, 401

(56) References Cited

FOREIGN PATENT DOCUMENTS

| DE | 37 19086 | 10/1988 |
|---|---|---|
| EP | 0 282 720 | 9/1988 |
| WO | WO 99/55953 | 11/1999 |
| WO | WO 01/25380 | 4/2001 |
| WO | WO 01/25381 | 4/2001 |
| WO | WO 01/25382 | 4/2001 |
| WO | WO 01/25385 | 4/2001 |

*Primary Examiner*—Shelley A. Dodson
(74) *Attorney, Agent, or Firm*—Scully, Scott, Murphy & Presser

(57) ABSTRACT

The present invention relates to UV-light-absorbing quaternary polysiloxanes that exert a care effect on natural or synthetic fibers, exhibit high substantivity to fibers, and offer protection against damage caused by UV-light. The UV-light-absorbing quaternary compounds can be used in formulations for textile care products and cosmetic, including skin and hair, products.

20 Claims, 3 Drawing Sheets

UV-LIGHT-ABSORBING QUATERNARY POLYSILOXANES

FIELD OF THE INVENTION

The present invention relates to UV-light-absorbing quaternary polysiloxanes, to processes for the preparation thereof and to the use of such UV-light-absorbing quaternary polysiloxanes in formulations for textile care and cosmetic preparations.

BACKGROUND OF THE INVENTION

It is well-known that UV (ultra-violet) light having wavelengths from 200 to 400 nm is responsible for the bleaching and the damage of textiles, synthetic fibers and natural fibers (e.g., wool, cotton and hair).

For this reason, there is a growing need for compounds which shield textiles, synthetic fibers and natural fibers from UV radiation, or permit control over the degree of damage caused by UV light.

It is therefore desirable to provide compounds which can exert control over the UV radiation to which the textiles or the synthetic or natural fibers are exposed.

The literature discloses a large number of compounds which are used for UV light protection of fibers, dyes and pigments. Such compounds are typically used directly in the preparation of the fibers.

However, these compounds do not have a caring or softening effect. In addition, the prior art compounds often lack adhesion to the surface of the fiber, which means that after just a few wash operations, the UV protection on the fibers is lost.

It is therefore desirable to provide compounds which are capable of: (i) exerting a care effect on natural or synthetic fibers, (ii) exhibiting high substantivity, i.e., high affinity, to the fibers resulting in an improved permanency, and (iii) offering protection against damage by mechanical and/or optical (e.g., UV light) effects. The term 'care effect' is used herein to denote a softening and/or conditioning effect, possibly in combination with a reduction in fiber damage after mechanical stress. Moreover, and in some embodiments, the term 'care effect' denotes an anti-wrinkle effect (easy ironing effect), improved elasticity and improved tear strength of the fabric.

In order to be able to provide adequate UV protection even after a number of washes, the compounds should also be able to be incorporated into fabric softener formulations and attach to the fibers during the fabric softener cycle.

Quaternary polysiloxanes are likewise known from the literature and are described, for example, in EP-A-0 282 720 and DE-A-37 19 086. Such compounds are known, in particular, for their conditioning properties in hair cosmetics and for their softening and care effects in textile treatment. Compounds of this type are also used in order to increase the elasticity and the tear strength of textiles and to reduce the formation of folds or creases thereof and/or to facilitate ironing later on ("easy ironing") (see, for example, WO-01/25385, WO-01/25382, WO-01/25381, WO-01/25380, WO-99/55953). Compounds as described in EP-282 720 and DE-37 19 086, however, do not exhibit protection against the harmful effect of UV radiation.

A disadvantage according to the prior art is therefore that in each case special compounds have to be provided in order to achieve the effects described above.

SUMMARY OF THE INVENTION

An object of the present invention is to provide compounds that can be used universally, which exert a smoothing, care and softening effect on natural or synthetic fibers, exhibit high affinity to the natural or synthetic fibers (e.g., wool, cotton or hair) or other surfaces (e.g., skin), and reduce damage by mechanical and/or optical effects (e.g., UV light).

Surprisingly, it was found that the abovementioned object is achieved by UV-light-absorbing quaternary polysiloxanes.

The present invention therefore provides UV-light-absorbing quaternary polysiloxanes of general formula (I)

$$\text{(I)}$$

$$R^2-\underset{\underset{R^1}{|}}{\overset{\overset{R^1}{|}}{Si}}O\left[\underset{\underset{R^2}{|}}{\overset{\overset{R^1}{|}}{SiO}}\right]_a\left[\underset{\underset{\underset{\underset{\underset{R^2}{|}}{\overset{\overset{R^1}{|}}{Si}-R^1}}{|}}{\overset{\overset{O}{|}}{\left[R^1-\overset{\overset{R^1}{|}}{Si}-R^2\right]_a}}}{\overset{\overset{R^1}{|}}{SiO}}\right]_b\left[\underset{\underset{R^2}{|}}{\overset{\overset{R^1}{|}}{SiO}}\right]_a\underset{\underset{R^1}{|}}{\overset{\overset{R^1}{|}}{Si}}-R^2$$

in which radicals $R^1$ are identical or different and are in each case lower alkyl radicals having 1 to 4 carbon atoms or phenyl radicals, $R^2$ is $R^1$ or a radical of formula (Ia)

$$R^2\!=\!-M\text{-}Z^+ A^- \qquad \text{(Ia)}$$

with the proviso that in the average molecule at least one radical $R^2$ is a radical of the formula -M-$Z^+$ $A^-$, wherein Z is a radical of formula (Ib)

$$\text{(Ib)}$$

$$-\underset{\underset{R^4}{|}}{\overset{\overset{R^3}{|}}{N^+}}-(CH_2)_{\overline{x}}-R^5,$$

$R^3$, $R^4$ are alkyl radicals having 1 to 22 carbon atoms or alkenyl radicals having 2 to 22 carbon atoms, in which the alkyl or alkenyl radicals can include hydroxyl groups, $R^5$ is a monovalent chromophore radical responsible for UV-absorption of formula (Ic)

$$\text{(Ic)}$$

$$-(R^6)_m-(R^7)_n-\!\!\!\bigcirc\!\!\!-(R^8)_o$$

in which
$R^6$ is $$-O-\overset{\overset{O}{\|}}{C}-, \quad -\underset{\underset{H}{|}}{N}-\overset{\overset{O}{\|}}{C}-, \quad \text{or} \quad -\underset{\underset{H}{|}}{N}\!=\!\overset{\overset{}{}}{C}-,$$

$R^7$ is —CH=CH—, $R^8$ are identical or different and in each case are hydrogen, alkyl, haloalkyl, halogen, phenyl, hydroxyl, alkoxy, amino, alkylamino, dialkylamino, di(hydroxyalkyl)amino or di(polyalkoxy)amino radicals, m=0 or 1,
n=0 or 1,
o=0 to 5,
x=0 to 6, M is a divalent hydrocarbon radical having at least 4 carbon atoms which has one hydroxyl group and which may be interrupted by one or more oxygen atoms, where the N atom of the radical Z is bonded to the radical M via the carbon atom adjacent to the C—OH group in the radical M, $A^-$ is an inorganic or organic anion which stems from a customary physiologically compatible acid HA, a, independently of the others, has a value from 1 to 200, and b has a value from 0 to 10.

The present invention further provides for the preparation of the compounds of formula (I) mentioned-above. The process according to the present invention comprises reacting compounds of general formula (II)

$$R^9-\underset{R^1}{\underset{|}{\overset{R^1}{\overset{|}{Si}}}}O-\left[\underset{R^9}{\underset{|}{\overset{R^1}{\overset{|}{Si}}}}O\right]_a-\left[\underset{\underset{\underset{R^1-Si-R^1}{\underset{|}{O}}}{\underset{|}{\overset{|}{O}}}}{\underset{|}{\overset{R^1}{\overset{|}{Si}}}}O\left[\underset{R^9}{\underset{|}{\overset{R^1}{\overset{|}{Si}}}-R^9}\right]_a\right]_b-\underset{R^9}{\underset{|}{\overset{R^1}{\overset{|}{Si}}}}O-\underset{R^1}{\underset{|}{\overset{R^1}{\overset{|}{Si}}}}-R^9 \quad (II)$$

in which the radicals $R^1$ are identical or different and in each case are lower alkyl radicals having 1 to 4 carbon atoms or phenyl radicals, $R^9$ is $R^1$ or a monovalent radical which corresponds to the structure of the radical M, where the radical $R^9$ has an epoxide group in place of the linkage to Z and the hydroxyl group, with the proviso that, in the average molecule, at least one radical $R^9$ is a monovalent radical which corresponds to the structure of the radical M, where the radical $R^9$ has an epoxide group in place of the linkage to Z and the hydroxyl group, a independently of the others, has a value from 1 to 200 and b has a value from 0 to 10, with tertiary amines of general formula (IIb)

$$\underset{R^4}{\underset{|}{\overset{R^3}{\overset{|}{N}}}}-(CH_2)_x-R^5 \quad (IIb)$$

wherein $R^3$, $R^4$ are alkyl radicals having 1 to 22 carbon atoms or alkenyl radicals having 2 to 22 carbon atoms, in which the alkyl or alkenyl radicals can include hydroxyl groups, $R^5$ is a monovalent chromophore radical responsible for the UV-absorption of formula (Ic)

$$-(R^6)_m-(R^7)_n-\bigcirc-(R^8)_o \quad (Ic)$$

in which $R^6$ is $$-O-\overset{O}{\overset{\|}{C}}-, \quad -\underset{H}{\underset{|}{N}}-\overset{O}{\overset{\|}{C}}-, \quad \text{or} \quad -N=\underset{H}{\underset{|}{C}}-,$$

$R^7$ is —CH=CH—, $R^8$ are identical or different and are in each case hydrogen, alkyl, haloalkyl, halogen, phenyl, hydroxyl, alkoxy, amino, alkylamino, dialkylamino, di(hydroxyalkyl)amino or di(polyalkoxy)amino radicals, m=0 or 1,
n=0 or 1,
o=0 to 5, and
x=0 to 6, in a manner known per se. Specifically, the reacting step is performed using quantitative ratios such that each epoxide group corresponds to at least one tertiary amino group. Moreover, the reacting step is carried out in the presence of a customary physiologically compatible organic or inorganic acid equivalent HA, based on nitrogen atom to be quaternized, and at a temperature of from 40° to 120° C.

DETAILED DESCRIPTION OF THE INVENTION

Figure 1:
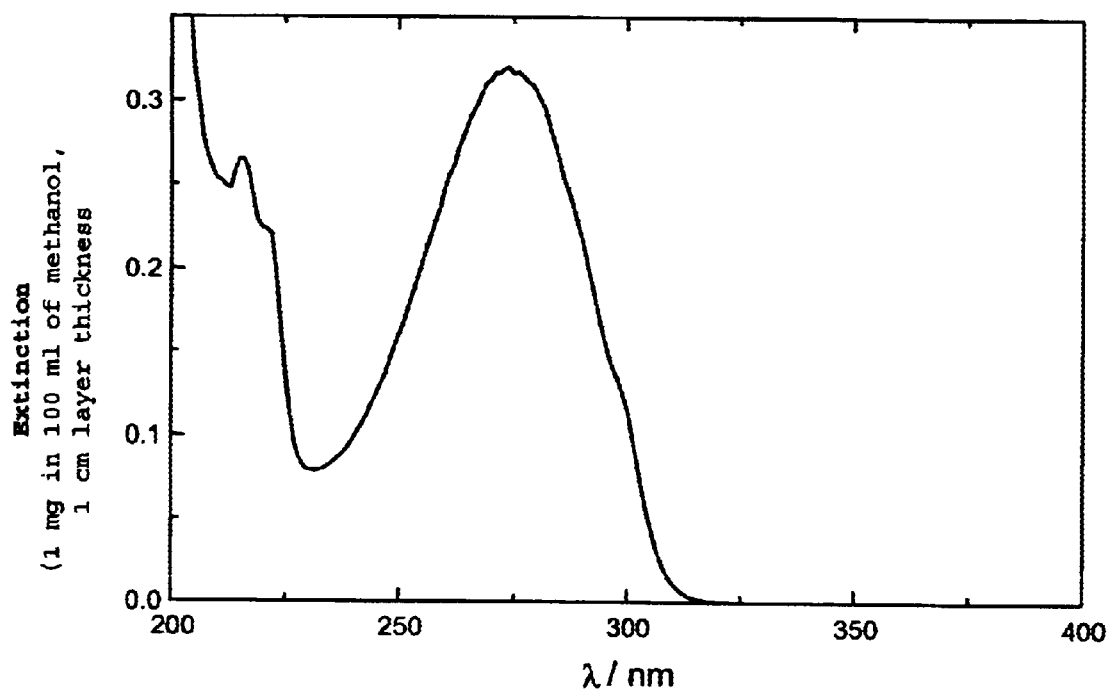
FIG. 1 is a UV-vis spectrum of the UV-light-absorbing quaternary polysiloxane compound of Example 1.

The present invention, which provides novel UV-light-absorbing quaternary polysiloxane compounds of formula (I) as well as a method of preparing such compounds, will now be described in more detail.

As stated above, the present invention provides UV-light-absorbing quaternary polysiloxane compounds of formula (I)

$$R^2-\underset{R^1}{\underset{|}{\overset{R^1}{\overset{|}{Si}}}}O-\left[\underset{R^2}{\underset{|}{\overset{R^1}{\overset{|}{Si}}}}O\right]_a-\left[\underset{\underset{\underset{R^1-Si-R^1}{\underset{|}{O}}}{\underset{|}{\overset{|}{O}}}}{\underset{|}{\overset{R^1}{\overset{|}{Si}}}}O\left[\underset{R^2}{\underset{|}{\overset{R^1}{\overset{|}{Si}}}-R^2}\right]_a\right]_b-\underset{R^2}{\underset{|}{\overset{R^1}{\overset{|}{Si}}}}O-\underset{R^1}{\underset{|}{\overset{R^1}{\overset{|}{Si}}}}-R^2 \quad (I)$$

wherein the variables $R^1$, $R^2$, a and b are as defined herein above.

Preferred examples of the radical $R^1$ are lower alkyl radicals having 1 to 4 carbon atoms, such as the methyl, ethyl, n-propyl, isopropyl or n-butyl radical, isobutyl radical, or phenyl radicals.

Preferred examples of the radical M, which is defined above as a divalent hydrocarbon radical having at least 4 carbon atoms which have one hydroxyl group and which may be interrupted by one or more oxygen atoms, where the N atom of the radical Z is bonded to the radical M via the carbon atom adjacent to the C—OH group in the radical M, include:

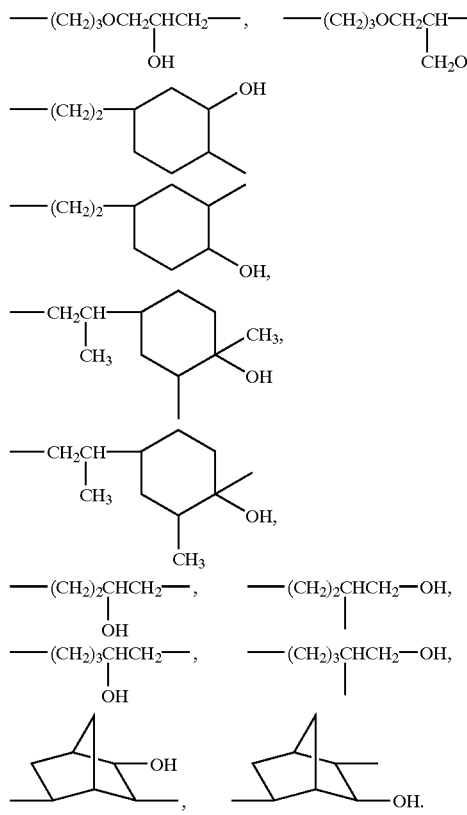

Within the compounds according to the present invention, the radicals Z may have identical or different meanings.

Preferred examples of the radical Z include:

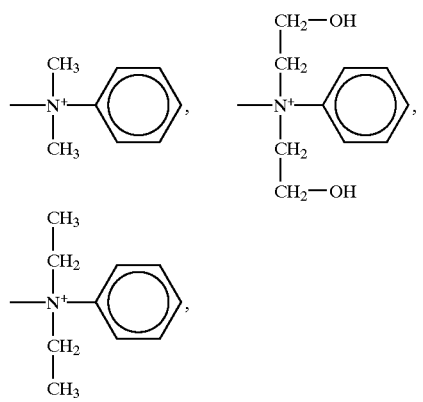

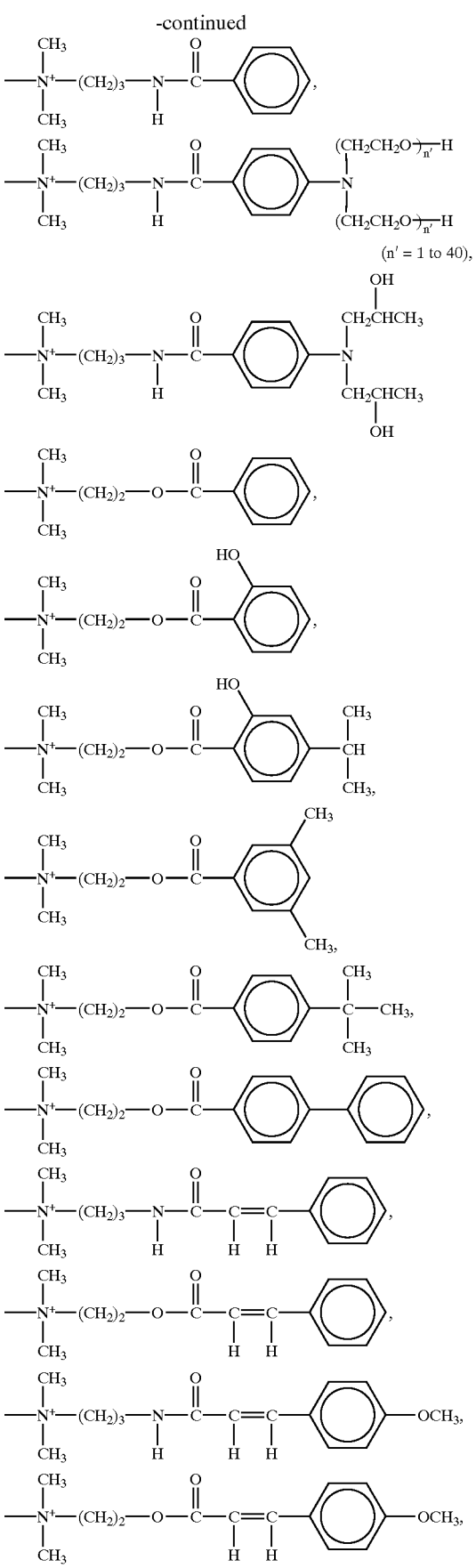

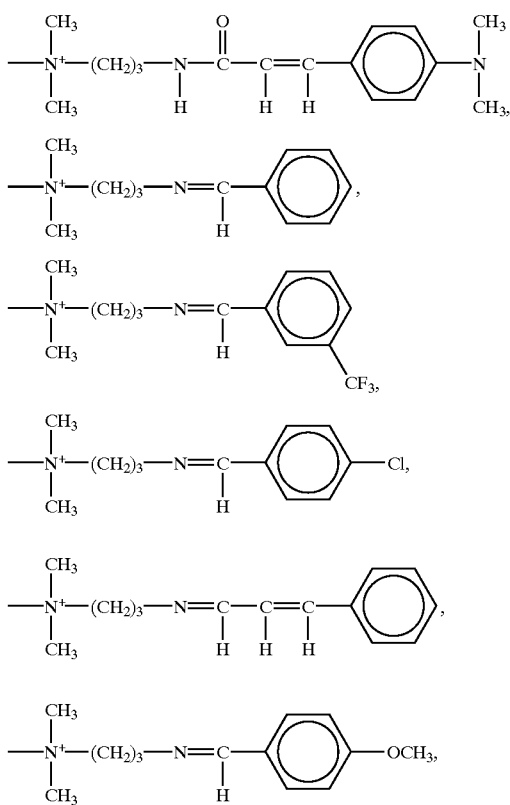

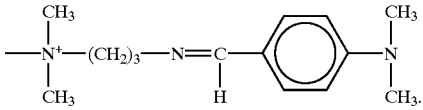

Preferred examples of A⁻, which is defined above as an inorganic or organic anion that stems from a customary physiologically compatible acid HA, are acetate, chloride, bromide, hydrogensulfate, sulfate, methosulfate, ethosulfate, citrate, tartrate and lactate ions, and anions of aromatic acids, such as the anions of p-toluenesulfonic acid, benzoic acid, salicylic acid, cinnamic acid, 4-methoxycinnamic acid, 4-aminobenzoic acid, 4-bis(hydroxypropyl)aminobenzoic acid, 4-bis(polyethoxy)aminobenzoic acid, 4-dimethylaminobenzoic acid, 3-imidazol-4-ylacrylic acid, 2-phenylbenzimidazole-5-sulfonic acid, 3,3'-(1,4-phenylenedimethine)bis(7,7-dimethyl-2-oxo-bicyclo[2.2.1]heptane-1-methanesulfonic acid), 2-hydroxy-4-methoxybenzophenone-5-sulfonic acid and 3-(4'-sulfo)benzylidenebornan-2-one.

A person skilled in the art is familiar with the fact that the compounds described above would be present in the form of a mixture with a distribution controlled essentially by the laws of statistics. The values for the indices a and b therefore represent average values.

Preferred examples of UV-light-absorbing quaternary polysiloxanes of the present invention are compounds of the following formulas:

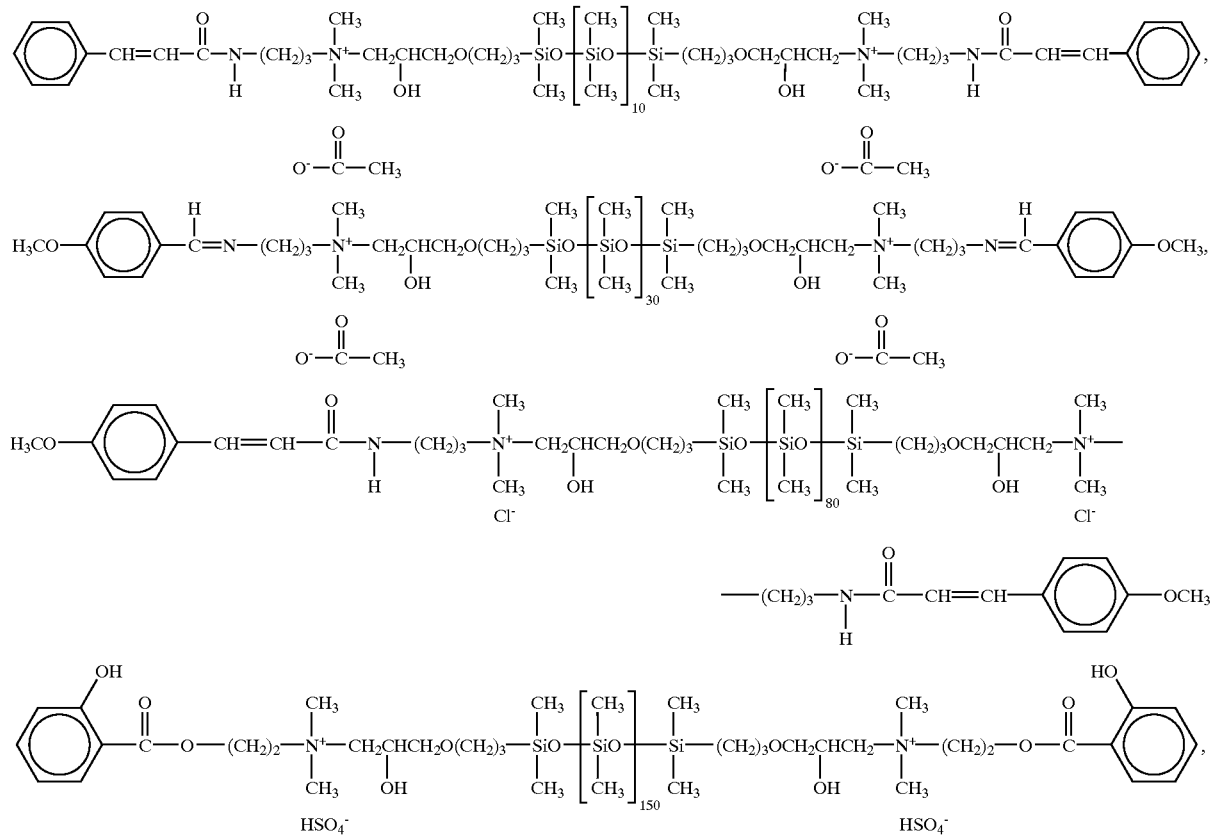

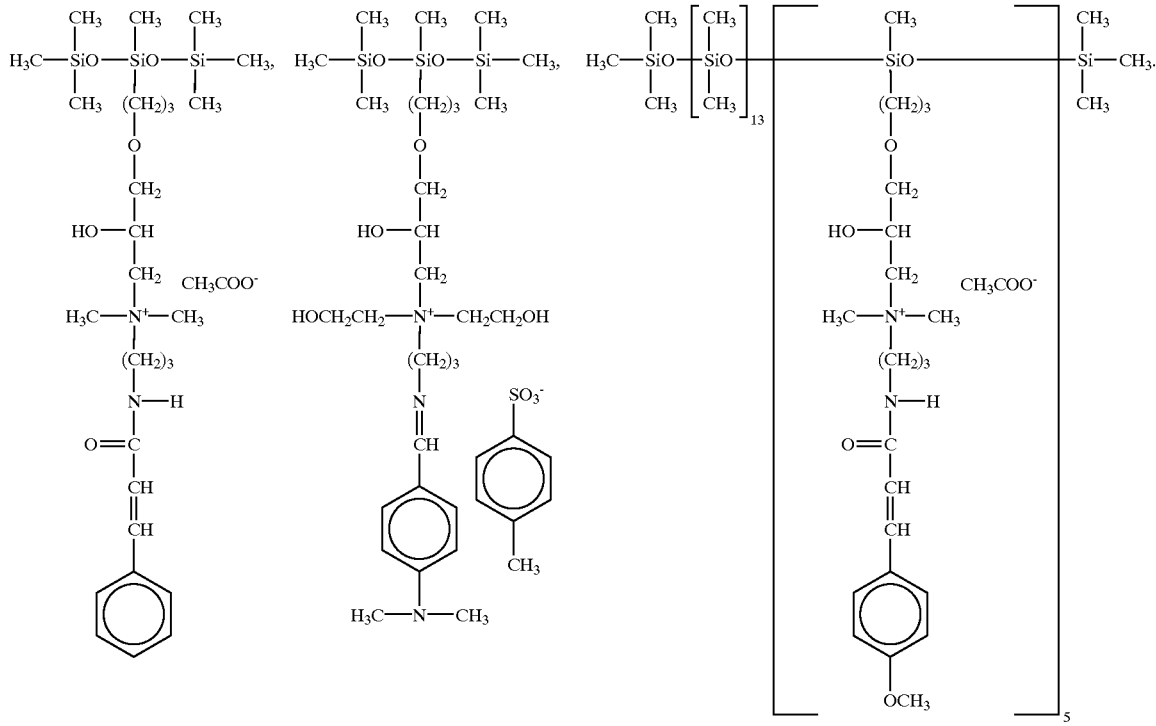

As stated above, the inventive compounds of formula (I) are suitable for use as an ingredient for use in various UV-light-absorbing formulations, including, but not limited to: UV-light-absorbing cosmetic formulations, UV-light-absorbing fabric softener formulations, UV-light-absorbing hair cleansing and care compositions as well as UV-light-absorbing skin protection, skin cleansing and/or skin care compositions. The various other ingredients used in such formulations besides the inventive UV-light-absorbing quaternary polysiloxanes are well-known to those skilled in the art.

The UV-light-absorbing quaternary polysiloxane compounds of formula (I) are prepared by reacting compounds of general formula (II), as defined above, with tertiary amines of general formula (IIb), as defined above, in a manner well known to those skilled in the art. The reaction of the present invention occurs using quantitative ratios of compounds of general formula (II) and (IIb) such that each epoxide group corresponds to at least one tertiary amino group. Moreover, the reaction of the present invention is carried out in the presence of a customary physiologically compatible organic or inorganic acid equivalent HA, based on the N atom being quaternized. The reaction is typically carried out at a temperature range from 40° to 120° C. A solvent or solvent system is generally used in the reaction described above.

Processes for the preparation of the compounds according to the present invention and the properties of these compounds are described in more detail in the examples below:

EXAMPLE 1

Preparation of a novel UV-light-absorbing quaternary polysiloxane of the general formula:

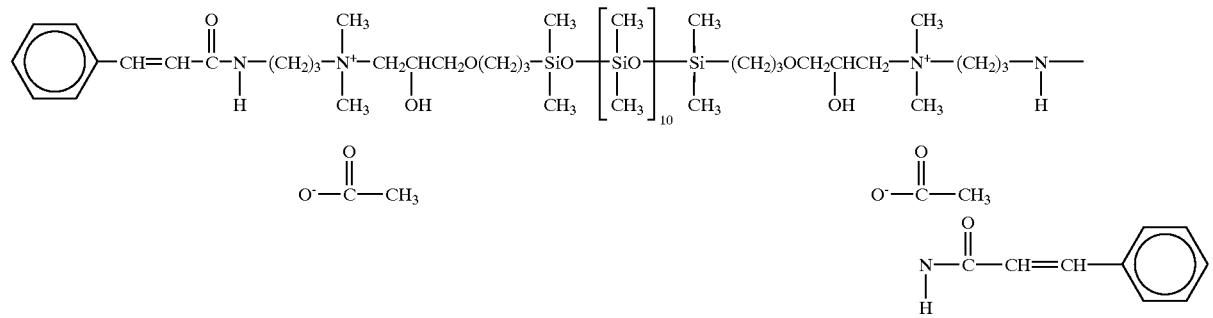

A 1 l four-necked flask provided with stirrer, dropping funnel, thermometer and reflux condenser was charged with 139.6 g (0.6 mol) of a tertiary amine of the general formula:

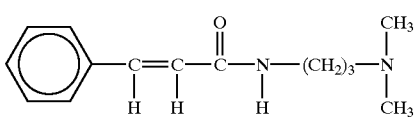

together with 36.3 g (0.6 mol) of acetic acid and 120 ml of isopropanol. After 30 minutes, 330 g (0.3 mol) of an epoxysiloxane of the general formula:

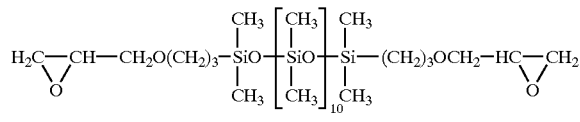

were added dropwise, heated to the reflux temperature and stirred for 6 hours. Distillation was then carried out under reduced pressure at a temperature of 100° C. A high-viscosity, yellow-brown product was obtained (quaternary nitrogen found: 1.4%; theor.: 1.7%.). FIG. 1 illustrates the UV-vis spectrum of the compound provided in this example.

EXAMPLE 2

Preparation of a novel UV-light-absorbing quaternary polysiloxanes of the general formula:

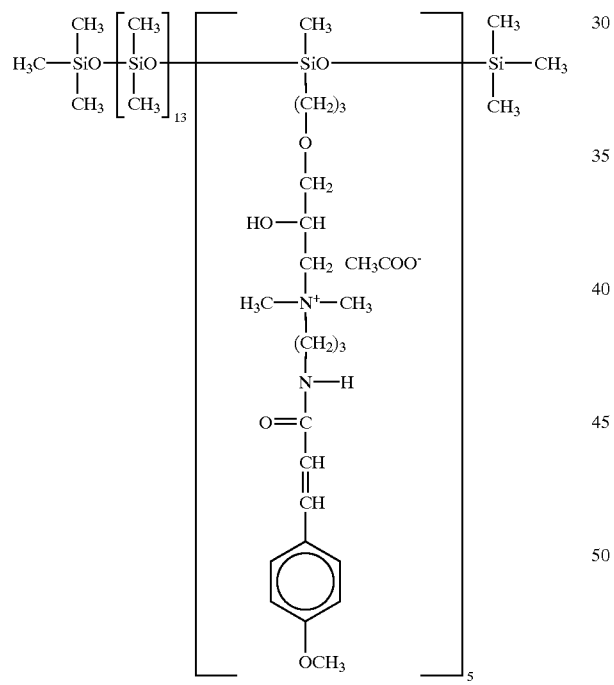

Figure 2:
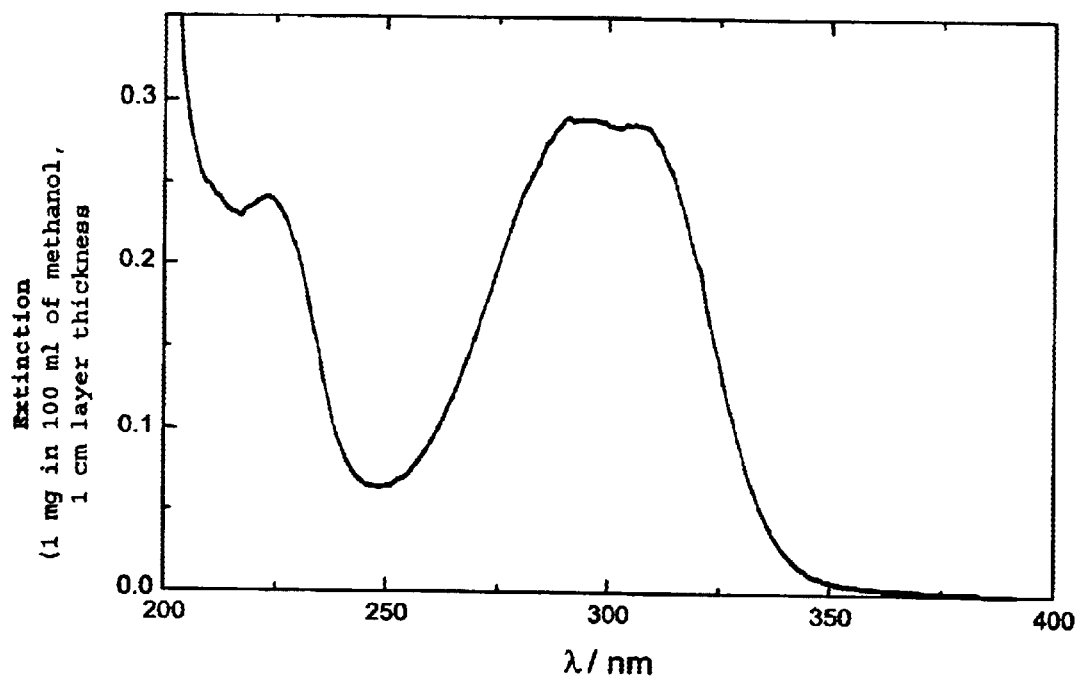
FIG. 2 is a UV-vis spectrum of the UV-light-absorbing quaternary polysiloxane compound of Example 2.

A 1 l four-necked flask provided with stirrer, dropping funnel, thermometer and reflux condenser was charged with 158.0 g (0.6 mol) of a tertiary amine of the general formula:

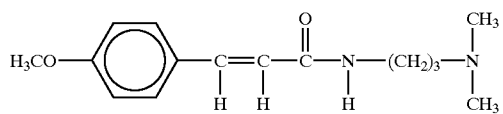

together with 36.3 g (0.6 mol) of acetic acid and 120 ml of isopropanol. After 30 minutes, 240 g (0.12 mol) of an epoxysiloxane of the general formula:

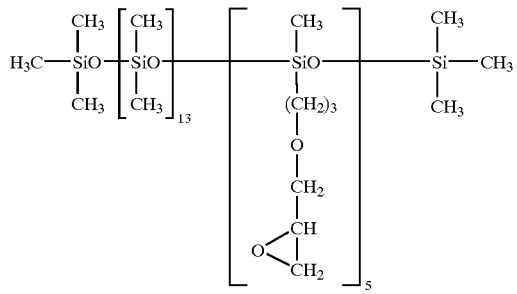

were added dropwise, heated to the reflux temperature and stirred for 6 hours. Distillation was then carried out under reduced pressure at a temperature of 100° C. A high-viscosity, yellow-brown product was obtained (quaternary nitrogen found: 1.65%; theor.: 1.9%.). FIG. 2 illustrates the UV-vis spectrum of the compound obtained from this example.

EXAMPLE 3

Preparation of a novel UV-light-absorbing quaternary polysiloxane of the general formula:

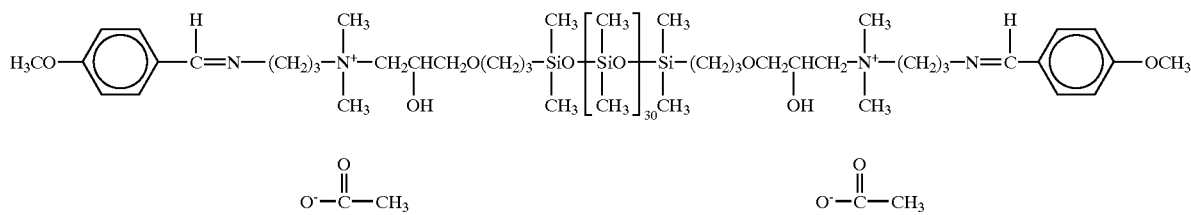

Figure 3:
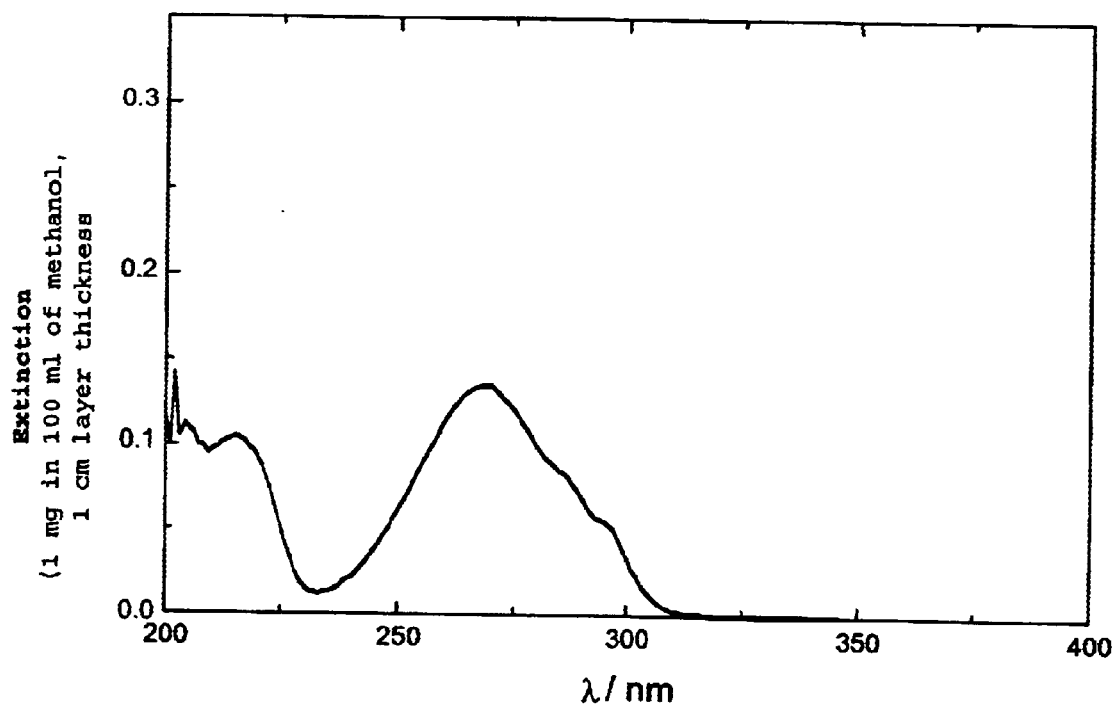
FIG. 3 is a UV-vis spectrum of the UV-light-absorbing quaternary polysiloxane compound of Example 3.

A 1.5 l four-necked flask provided with stirrer, dropping funnel, thermometer and reflux condenser was charged with 132.0 g (0.6 mol) of a tertiary amine of the general formula:

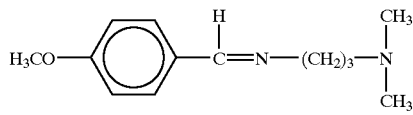

together with 36.3 g (0.6 mol) of acetic acid and 120 ml of isopropanol. After 30 minutes, 774 g (0.3 mol) of an epoxysiloxane of the general formula:

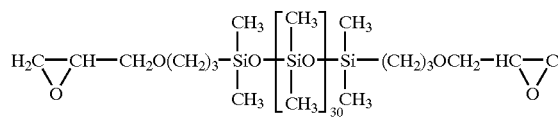

were added dropwise, heated to the reflux temperature and stirred for 6 hours. Distillation was then carried out under reduced pressure at a temperature of 100° C. A high-viscosity, yellow-brown product was obtained (quaternary nitrogen found: 0.7%; theor.: 0.9%.). The UV-vis spectrum of the compound obtained from this example is shown in FIG. 3.

EXAMPLE 4

Performance comparison:

For the performance comparison, the following novel UV-light-absorbing quaternary polysiloxanes were used:

Compound 1:

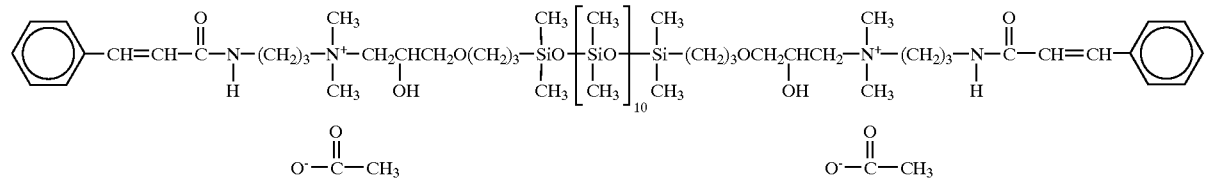

Compound 2:

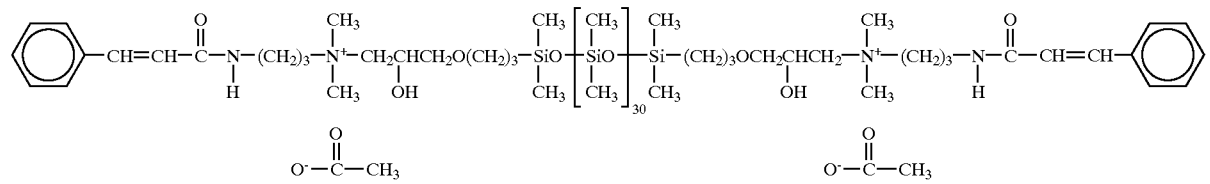

Compound 3:

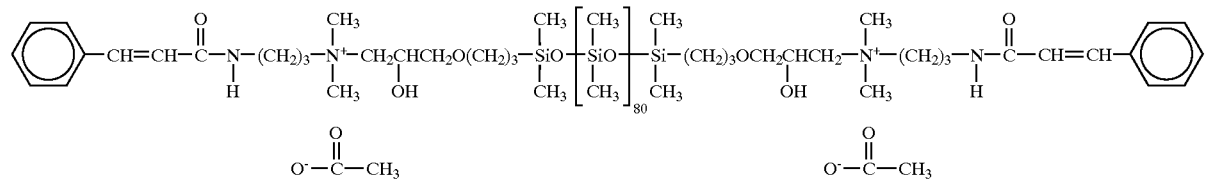

Compound 4:

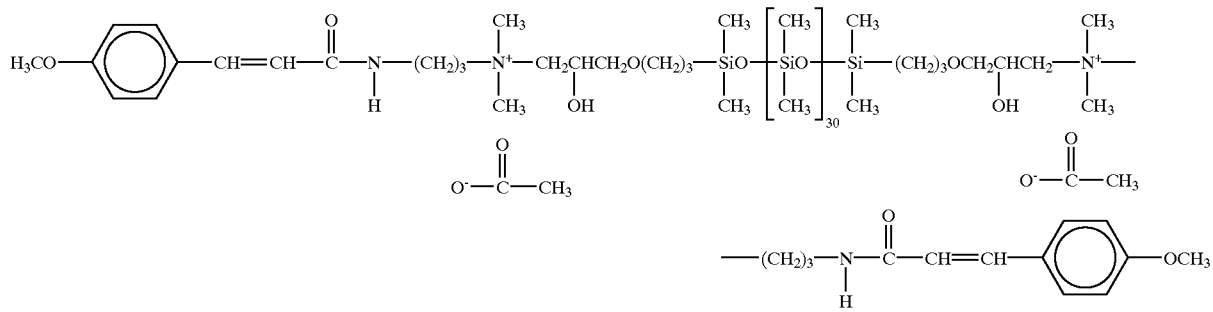

Compound 5:

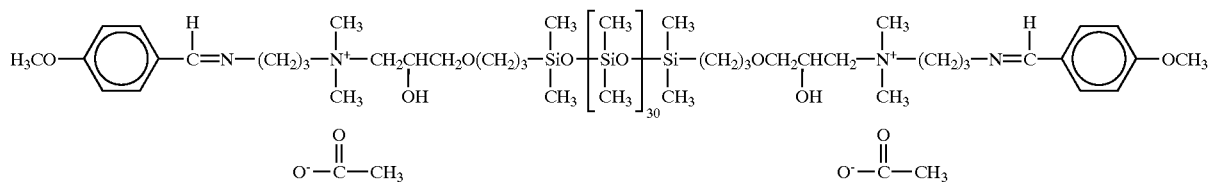

-continued

Compound 6:

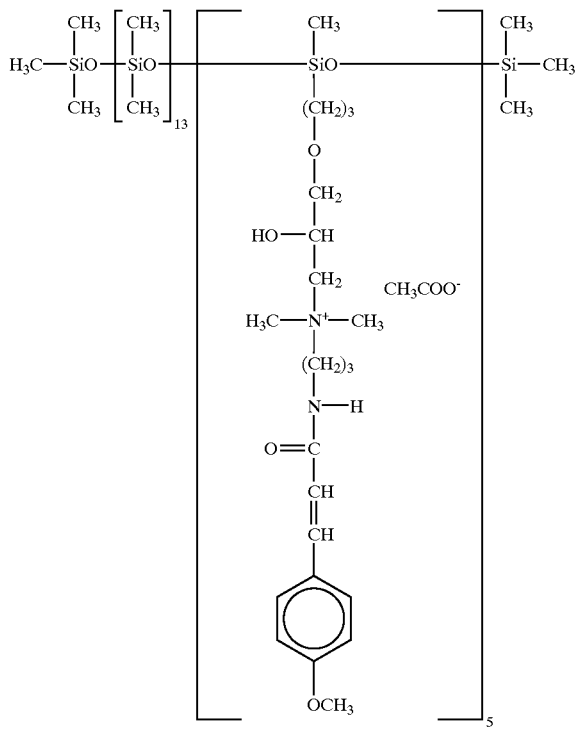

Compound 7:

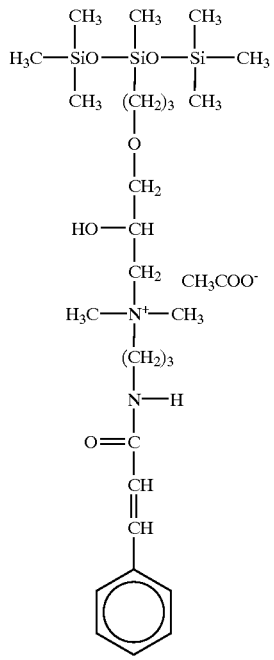

Preparation and testing of hair-treatment compositions using the novel compounds 1 to 6:

For the performance assessment, hair tresses which are used for sensory tests were predamaged in a standardized manner by a permanent waving treatment and a bleaching treatment. Customary hairdressing products were used for this purpose.

Materials:

permanent waving liquid (e.g., "ondi", Wella)

neutralizer (e.g., "neutrafix", Wella)

bleaching powder (e.g., "blondor special", Wella)

$H_2O_2$ (e.g., "Welloxyd 9%", Wella)

shampoo without care component (e.g., sodium lauryl ether sulfate (12% washing-active substance, NaCl thickened))

beakers hair coloring brush

The treatment was carried out in the following order:

1. Permanent waving treatment:

The hair tresses were moistened with the permanent waving liquid (weight ratio of hair: liquid=1:2). After a contact time of 15 minutes at room temperature in a covered beaker, the permanent waving liquid was carefully rinsed out for 2 min.

The hair tresses were then gently pressed using a hand towel. The neutralizer (ratio of hair: liquid=1:2) had a contact time of 10 minutes at room temperature. The neutralizer was then carefully rinsed out for 2 minutes. The hair was then dried overnight at room temperature.

2. Bleaching treatment:

The bleaching powder and the $H_2O_2$ were formulated to give a paste (weight ratio of powder: $H_2O_2$=2:3). The paste was then immediately applied to the perm-treated hair using a brush. The contact time was 30 minutes at room temperature. The bleaching paste was then rinsed out under running water for 2 minutes.

The hair was then washed with a shampoo without conditioner for 1 minute (amount of shampoo: 0.5 ml/hair tress) and then rinsed out for 1 minute. Before being used for the sensory tests, the predamaged hair tresses were dried overnight at room temperature.

Test formulation:

The conditioning products were tested in a simple hair rinse having the following composition:

| Product | Proportion by weight |
|---|---|
| TEGINACID ® C | 0.5% |
| Ceteareth-25 | |
| TEGO ® Alkanol 16 | 2.0% |
| Cetyl Alcohol | |
| "Conditioner" | 2.0% |
| Water | ad. 100% |
| Citric acid | ad. pH 4.0 ± 0.3 |

"Conditioners" is the term used herein to refer to the compound examples according to the present invention.

Standardized treatment of predamaged hair tresses with conditioning samples:

The hair tresses predamaged, as described above, were treated as follows with the above-described conditioning rinse:

The hair tresses were wetted under running warm water. The excess water was gently squeezed out by hand, then the rinse was applied and gently worked into the hair (1 ml/hair tress (2 g)). After a contact time of 1 minute, the hair was rinsed for 1 minute.

Prior to the sensory assessment, the hair was dried in the air at 50% atmospheric humidity and 25° C. for at least 12 h.

Assessment criteria:

The sensory evaluations were made using grades given on a scale from 1 to 5, 1 being the poorest evaluation and 5 being the best evaluation.

Wet combability:

| Evaluation | Toothing of the comb | Result |
|---|---|---|
| 5 | coarse | No knots, the hair can be detangled easily |
|   | fine | Very easy to comb through, no resistance detectable |
| 4 | coarse | Individual knots. The hair can be detangled easily |
|   | fine | Easy to comb through, slight resistance detectable |
| 3 | coarse | A few knots, slight resistance |
|   | fine | Some degree of resistance detectable, which decreases after repeated combing |
| 2 | coarse | Some knots, notable resistance |
|   | fine | Notable resistance which does not decrease after repeated combing |
| 1 | coarse | Many knots, severe resistance |
|   | fine | Very severe resistance, sometimes the hair cannot be combed through |

Wet feel:

| Evaluation | Result |
|---|---|
| 5 | Very smooth, soft but nevertheless beautifully strong, of good feel, not greasy/tacky (no residues detectable) |
| 4 | Smooth and soft and/or only slight residues detectable |
| 3 | Smooth, somewhat hard and/or some residues detectable |
| 2 | Hard and/or notable greasy, waxy residues |
| 1 | Very hard, rough, harsh and/or extremely greasy, tacky (clearly detectable greasy, waxy residues detectable) |

Dry combability:

| Evaluation | Toothing of the comb | Result |
|---|---|---|
| 5 | coarse | No knots, the hair can be detangled easily |
|   | fine | Very easy to comb through, no resistance detectable, the hair does not become charged |
| 4 | coarse | Individual knots. The hair can be detangled easily |
|   | fine | Easy to comb through, low resistance detectable, the hair becomes charged to a minimum degree |
| 3 | coarse | A few knots, slight resistance |
|   | fine | Some resistance detectable which decreases after repeated combing, the hair becomes slightly charged |
| 2 | coarse | Some knots, notable resistance |
|   | fine | Notable resistance which does not decrease after repeated combing, the hair becomes charged |
| 1 | coarse | Many knots, severe resistance |
|   | fine | Very severe resistance, sometimes the hair cannot be combed through, the hair becomes considerably charged |

Dry feel:

| Evaluation | Result |
|---|---|
| 5 | Very smooth, soft but nevertheless strong, full, of good feel |
| 4 | Smooth and soft |
| 3 | Smooth, slightly hard and/or slightly harsh (residues) |
| 2 | Hard, somewhat harsh |
| 1 | Rough, hard, dry, harsh (residues) |

Dry appearance:

| Evaluation | Result |
|---|---|
| 5 | Extremely shiny |
| 4 | Shiny |
| 3 | Somewhat shiny |
| 2 | Slightly shiny, slightly harsh |
| 1 | Harsh, no shine |

Volume:

In order to assess the volume, the hair locks were shaken gently by holding them at the bonding point.

| Evaluation | Result |
|---|---|
| 5 | Loose, bulky drop, ⌀ (i.e., diameter) in the tip area rel. large |
| 4-2 | Intermediate stages |
| 1 | Hair hangs heavily downward, ⌀ below the bundling similar to the tip area |

In Table 1 below, the results of the sensory assessment of the treatment of hair tresses carried out as described above with substances according to the present invention and placebo were compared.

TABLE 1

| Examples according to the invention | Detangling | Wet combability | Wet feel | Dry combability | Dry feel | Shine | Volume |
|---|---|---|---|---|---|---|---|
| Compound 3 | 4.5 | 5 | 4 | 4.5 | 4.0 | 3.75 | 1.75 |
| Compound 4 | 4.5 | 4.5 | 3.75 | 4 | 4.25 | 3.75 | 1.5 |
| Compound 2 | 3.5 | 4 | 3.75 | 4 | 3.75 | 3.5 | 1.75 |
| Compound 5 | 4 | 3.75 | 4.25 | 3.75 | 3.75 | 3.75 | 1.5 |
| Compound 1 | 3.5 | 3.5 | 4 | 3.5 | 3.5 | 3.5 | 2 |
| Compound 6 | 3.5 | 3.25 | 3.5 | 3.5 | 3.25 | 3.5 | 2 |
| Placebo | 1.5 | 1.25 | 1.75 | 2.25 | 2.75 | 3.25 | 2.5 |

It was found that the compound examples according to the present invention receive very good cosmetic evaluations in the sensory assessment.

EXAMPLE 5

Testing of textile fabric softeners using compounds 1 to 7 according to the present invention:

To test the softness and the UV protective action on textile fabrics, standard commercial ester quats (e.g. Rewoquat® WE 18) were used to prepare 18% strength fabric softener formulations which in each case comprise between 1% and 5% additions of compounds 1 to 6. The softness was measured on standard commercial cotton terry fabric and the UV protective action was measured on colored test fabrics in accordance with USTM standards. The test dyes used were Direct Blue 1 (DB 1), Direct Blue 90 (DB 90) and Acid Red 151 (AR 151).

The formulations with the additions of compounds 1 to 6 should have a positive effect on the softness of the fabric, a neutral behavior also would be acceptable. A negative effect on the softness leads to a drop in the overall assessment.

The use concentration of all fabric softener formulations was analogous to a normal domestic washing machine, 0.025%.

Following application, the terry fabrics were assessed by a panel consisting of 10 trained people with regard to its soft hand.

All silicon-containing formulations were compared directly against the softness of laundry without UV-light-absorbing quaternary polysiloxanes (only Rewoquat® WE 18). In this regard, (1)=very soft and (5)=hard. The results are summarized in Table 2.

The dyed test fabrics were irradiated for 4 weeks with a 1000 watt lamp, the spectrum of which largely corresponding to that of natural sunlight.

The color values (E) of the dyed fabric swatches were measured before and after irradiation by means of a color measurement instrument. Table 2 gives the differences in the color values (ΔE) in each case before and after irradiation.

TABLE 2

| | Polysiloxane | | Color change ΔE | | |
|---|---|---|---|---|---|
| Compounds | content | Soft hand | DB 1 | DB 90 | AR 151 |
| WE 18 | / | 2.0 | 7.4 | 5.9 | 4.9 |
| 1 | 1% | 2.2 | 1.4 | 1.3 | 1.4 |
| 1 | 3% | 2.1 | 0.9 | 0.6 | 0.6 |
| 1 | 5% | 1.9 | 0.7 | 0.5 | 0.4 |
| 2 | 1% | 1.6 | 2.9 | 2.6 | 2.1 |
| 2 | 3% | 1.5 | 2.1 | 2.0 | 1.5 |
| 2 | 5% | 1.7 | 1.6 | 1.2 | 0.9 |
| 3 | 1% | 1.4 | 4.7 | 4.3 | 4.1 |
| 3 | 3% | 1.3 | 3.8 | 3.6 | 3.4 |

TABLE 2-continued

| | Polysiloxane | | Color change ΔE | | |
|---|---|---|---|---|---|
| Compounds | content | Soft hand | DB 1 | DB 90 | AR 151 |
| 3 | 5% | 1.5 | 3.0 | 2.8 | 2.1 |
| 4 | 1% | 1.6 | 2.7 | 2.5 | 2.2 |
| 4 | 3% | 1.4 | 2.0 | 1.8 | 1.4 |
| 4 | 5% | 1.8 | 1.5 | 1.3 | 0.9 |
| 5 | 1% | 1.4 | 4.5 | 4.4 | 3.8 |
| 5 | 3% | 1.4 | 3.5 | 3.8 | 3.4 |
| 5 | 5% | 1.6 | 2.8 | 3.0 | 2.0 |
| 6 | 1% | 2.1 | 1.5 | 1.0 | 1.3 |
| 6 | 3% | 2 | 1.0 | 0.7 | 0.7 |
| 6 | 5% | 2 | 0.7 | 0.4 | 0.4 |
| 7 | 1% | 2 | 1.3 | 1.2 | 1.4 |
| 7 | 3% | 2.2 | 0.9 | 0.7 | 0.6 |
| 7 | 5% | 2.2 | 0.7 | 0.4 | 0.5 |

It is evident that the compounds according to the present invention improve the softness compared with the standard WE 18 and exert control over damaging UV radiation.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A UV-light-absorbing quaternary polysiloxane of general formula (I)

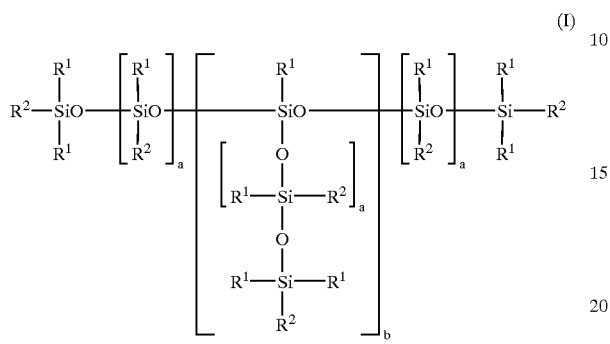

in which the radicals $R^1$ are identical or different and are in each case lower alkyl radicals having 1 to 4 carbon atoms or phenyl radicals, $R^2$ is $R^1$ or a radical of formula (Ia)

$R^2 = -M-Z^+ A^-$ (Ia)

with the proviso that, in the average molecule, at least one radical $R^2$ is a radical of the formula $-M-Z^+ A^-$, in which Z is a radical of formula (Ib)

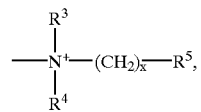
(Ib)

$R^3$, $R^4$ are alkyl radicals having 1 to 22 carbon atoms or alkenyl radicals having 2 to 22 carbon atoms, in which the alkyl or alkenyl radicals can include hydroxyl groups, $R^5$ is a monovalent chromophore radical responsible for UV-absorption of formula (Ic)

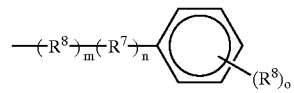
(Ic)

in which
$R^6$ is

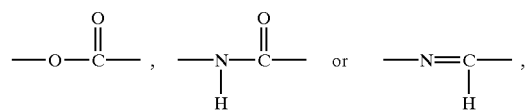

$R^7$ is $-CH=CH-$,
$R^8$ are identical or different and in each case are hydrogen, alkyl, haloalkyl, halogen, phenyl, hydroxyl, alkoxy, amino, alkylamino, dialkylamino, di(hydroxyalkyl)amino or di(polyalkoxy)amino radicals, m=0 or 1,
n=0 or 1,
o=0 to 5,
x=0 to 6, M is a divalent hydrocarbon radical having at least 4 carbon atoms which has one hydroxyl group and which may be interrupted by one or more oxygen atoms, where the N atom of the radical Z is bonded to the radical M via the carbon atom adjacent to the C—OH group in the radical M, $A^-$ is an inorganic or organic anion which stems from a customary physiologically compatible acid HA, a, independently, has a value from 1 to 200, and b has a value from 0 to 10.

2. The UV-light-absorbing compound of claim 1, wherein R is a methyl, ethyl, n-propyl, isopropyl, n-butyl radical, or isobutyl radical.

3. The UV-light-absorbing compound of claim 1, wherein $R^1$ is a phenyl radical.

4. The UV-light-absorbing compound of claim 1, wherein M is identical or different to one of the radicals selected from the group consisting of

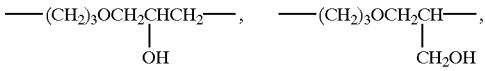

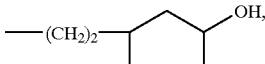

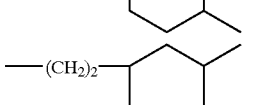

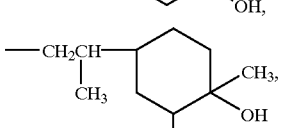

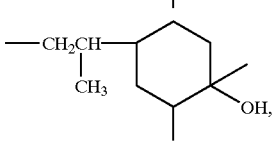

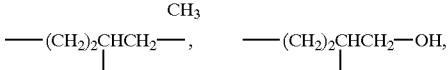

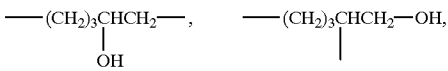

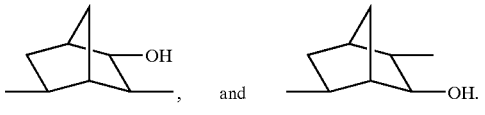

5. The UV-light-absorbing compound of claim 1, wherein Z is identical or different to one of the radicals selected from the group consisting of

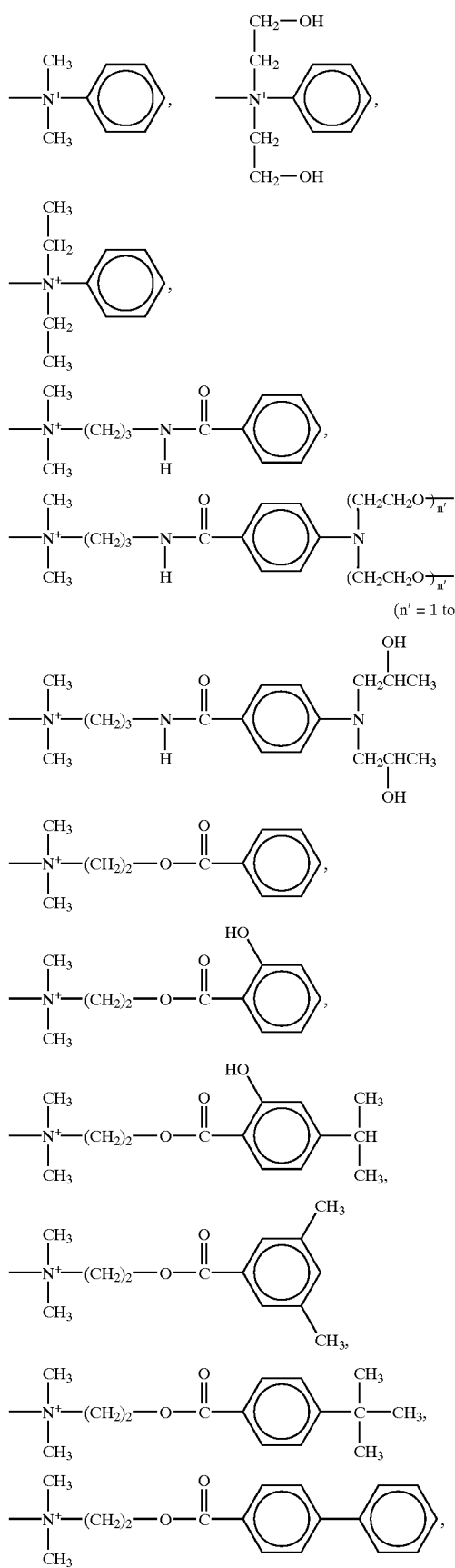

6. The UV-light-absorbing compound of claim 1, wherein A⁻ is identical or different to one of the radicals selected from the group consisting of acetate, chloride, bromide, hydrogensulfate, sulfate, methosulfate, ethosulfate, citrate, tartrate and lactate ions, and anions of aromatic acids.

7. The UV-light-absorbing compound of claim 6, wherein the anions of aromatic acids are selected from the group consisting of anions of p-toluenesulfonic acid, benzoic acid, salicylic acid, cinnamic acid, 4-methoxycinnamic acid, 4-aminobenzoic acid, 4-bis(hydroxypropyl)aminobenzoic acid, 4-bis(polyethoxy)aminobenzoic acid, 4-dimethylaminobenzoic acid, 3-imidazol-4-ylacrylic acid, 2-phenylbenzimidazole-5-sulfonic acid, 3,3'-(1,4-phenylenedimethine)bis (7,7-dimethyl-2-oxo-bicyclo[2.2.1] heptane-1-methanesulfonic acid), 2-hydroxy-4-methoxybenzophenone-5-sulfonic acid and 3-(4'-sulfo) benzylidenebornan-2-one.

8. A UV-light-absorbing compound of the formula
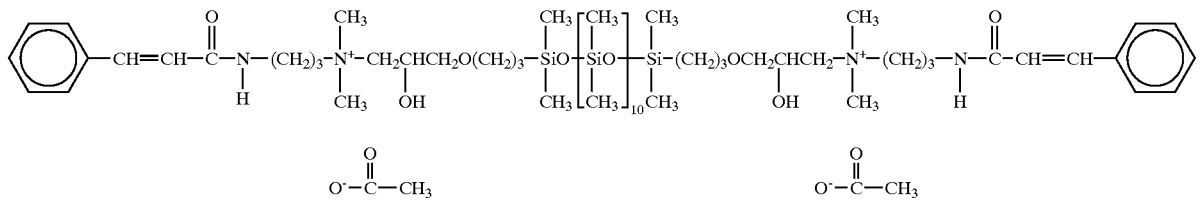
9. A UV-light-absorbing compound of the formula
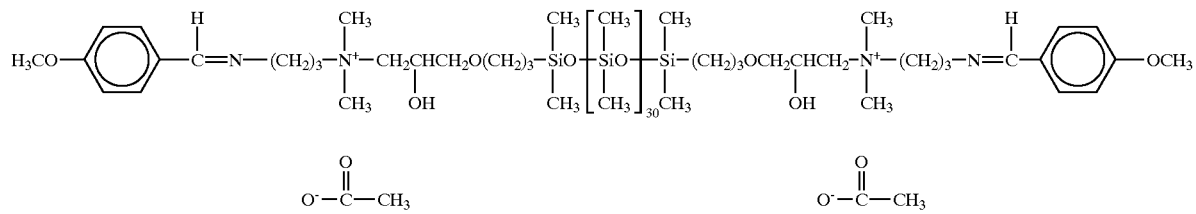
10. A UV-light-absorbing compound of the formula
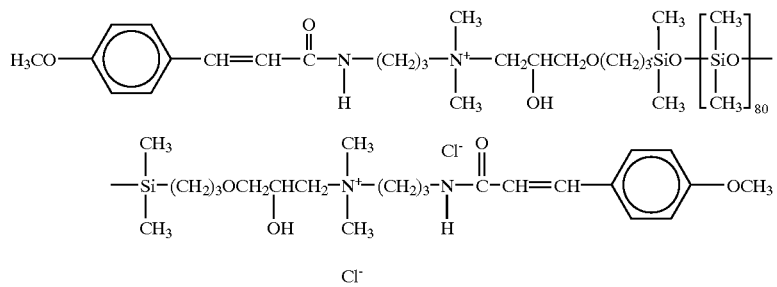
11. A UV-light-absorbing compound of the formula
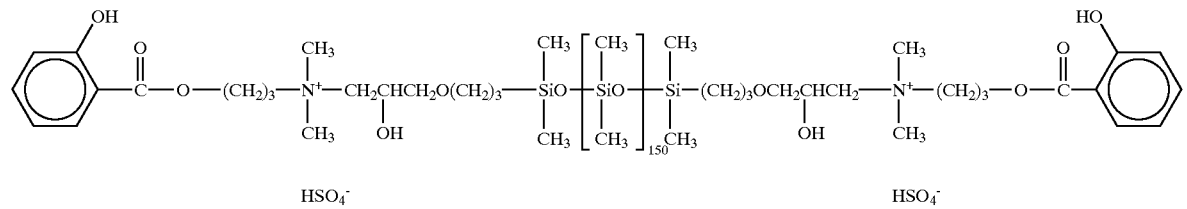
12. A UV-light-absorbing compound of the formula
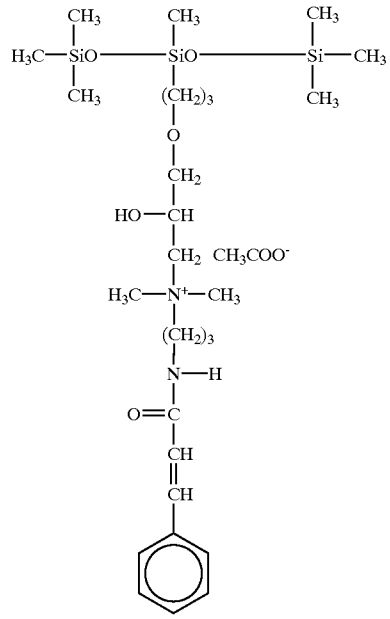
13. A UV-light-absorbing compound of the formula
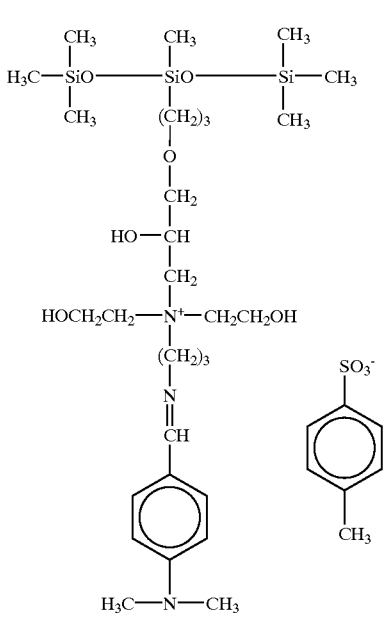

14. A UV-light-absorbing compound of the formula

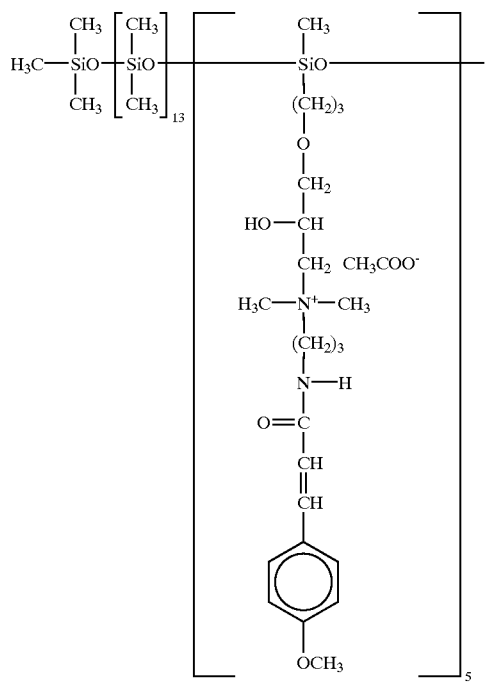

15. A process for the preparation of UV-light-absorbing compounds, which comprises reacting compounds of general formula (II)

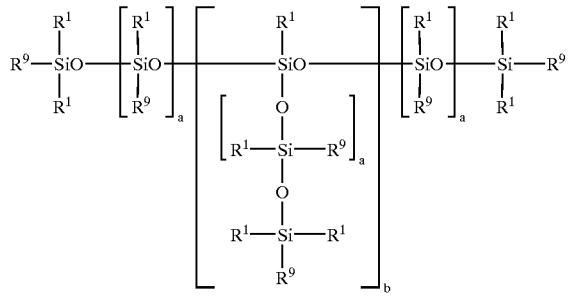

in which the radicals $R^1$ are identical or different and in each case are lower alkyl radicals having 1 to 4 carbon atoms or phenyl radicals, $R^9$ is $R^1$ or a monovalent radical which corresponds to the structure of the radical M, where the radical $R^9$ has an epoxide group in place of the linkage to Z and the hydroxyl group, with the proviso that, in the average molecule, at least one radical $R^9$ is a monovalent radical which corresponds to the structure of the radical M, where the radical $R^9$ has an epoxide group in place of the linkage to Z and the hydroxyl group, a independently of the others, has a value from 1 to 200 and b has a value from 0 to 10, with tertiary amines of general formula (IIb)

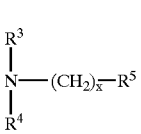

in which $R^3$, $R^4$ are alkyl radicals having 1 to 22 carbon atoms or alkenyl radicals having 2 to 22 carbon atoms, in which the alkyl or alkenyl radicals can include hydroxyl groups, $R^5$ is a monovalent chromophore radical responsible for the UV-absorption of formula (Ic)

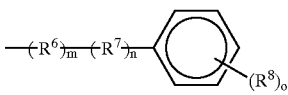

in which
$R^6$ is

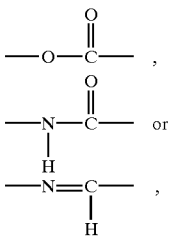

$R^7$ is —CH=CH—, $R^8$ are identical or different and are in each case hydrogen, alkyl, haloalkyl, halogen, phenyl, hydroxyl, alkoxy, amino, alkylamino, dialkylamino, di(hydroxyalkyl)amino or di(polyalkoxy)amino radicals, m=0 or 1, n=0 or 1, o=0 to 5, and x=0 to 6, in quantitative ratios such that each epoxide group corresponds to at least one tertiary amino group and carrying out the reaction in the presence of a physiologically compatible organic or inorganic acid equivalent HA, based on nitrogen atom to be quaternized, and at temperatures of from 40° to 120° C.

16. A UV-light-absorbing formulation comprising at least one UV-light-absorbing compound of claim 1.

17. The UV-light-absorbing formulation of claim 16 further comprising at least one cosmetic ingredient.

18. The UV-light-absorbing formulation of claim 16 further comprising at least one fabric softener ingredient.

19. The UV-light-absorbing formulation of claim 16 further comprising at least one hair cleansing or hair care ingredient.

20. The UV-light-absorbing formulation of claim 16 further comprising at least one skin protection, skin cleansing, or skin care ingredient.

* * * * *